United States Patent [19]

Blackmer et al.

[11] Patent Number: 4,953,546
[45] Date of Patent: * Sep. 4, 1990

[54] METHOD AND APPARATUS FOR PULMONARY AND CARIOVASCULAR CONDITIONING OF THE YOUNG OF LARGE ANIMALS

[75] Inventors: Richard H. Blackmer, Scotia; Jonathan W. Hedman, Burnt Hills, both of N.Y.

[73] Assignee: Transpirator Technologies, Inc., Somerset, N.J.

[ * ] Notice: The portion of the term of this patent subsequent to Feb. 2, 2005 has been disclaimed.

[21] Appl. No.: 295,656

[22] Filed: Jan. 10, 1989

Related U.S. Application Data

[63] Continuation-in-part of Ser. No. 841,300, Mar. 19, 1986, which is a continuation-in-part of Ser. No. 755,562, Jul. 16, 1985, Pat. No. 4,722,334.

[51] Int. Cl.[5] .............................................. A61M 16/00
[52] U.S. Cl. ........................... 128/203.16; 128/203.17; 128/203.26; 128/203.27; 128/204.17
[58] Field of Search ....................... 128/200.14, 200.16, 128/200.18, 200.21, 203.16, 203.17, 203.26, 203 A, 204.17

[56] References Cited

U.S. PATENT DOCUMENTS

| | | | |
|---|---|---|---|
| 2,091,034 | 8/1937 | Duncan | 128/203.27 |
| 3,638,926 | 2/1972 | Melville et al. | 128/203.27 |
| 3,863,630 | 2/1975 | Cavallo | 128/203.27 |
| 4,038,980 | 8/1977 | Fodor | 128/203.27 |
| 4,201,204 | 5/1980 | Rinne et al. | 128/203.27 |
| 4,319,566 | 3/1982 | Hayward et al. | 128/201.17 |
| 4,369,777 | 1/1983 | Lwoff et al. | 128/200.14 |
| 4,381,267 | 4/1983 | Jackson | 261/164 |
| 4,461,114 | 8/1983 | Lwoff et al. | 128/200.14 |
| 4,722,334 | 2/1988 | Blackmer et al. | 128/204.17 |

Primary Examiner—Randall L. Green
Assistant Examiner—K. M. Reichle
Attorney, Agent, or Firm—Kane, Dalsimer, Sullivan, Kurucz, Levy, Eisele and Richard

[57] ABSTRACT

An method and apparatus for delivering a humidified stream of gas to a young animal's respiratory tract. The gas is delivered at a dew point temperature greater than the ambient dew point temperature. The apparatus is especially useful in the treatment of foal pneumonia.

11 Claims, 5 Drawing Sheets

METHOD AND APPARATUS FOR PULMONARY AND CARIOVASCULAR CONDITIONING OF THE YOUNG OF LARGE ANIMALS

BACKGROUND OF THE INVENTION

1. Cross-Reference to Related Applications

This application is a continuation-in-part of co-pending U.S. application Ser. No. 841,300 filed 03-19-86 which is a continuation-in-part of co-pending U.S. application Ser. No. 755,562 filed July 16, 1985, now U.S. Pat. No. 4,722,334. The invention of the present application improves upon the invention of U.S. application Ser. No. 755,562 in that it provides an apparatus and method for the treatment of young animals with a much faster heat up time and at the same time is simpler in design and less expensive. The apparatus of the present invention also contains numerous safety features which will become obvious.

2. Field of the Invention

A high-humidity method and an apparatus are described which are useful for conditioning the respiratory pulmonary and/or a cardiovascular system in young animals. More particularly a method and an apparatus which are useful for delivering a therapeutic stream of humidified gas to a foal's respiratory tract at a dew point temperature greater than the ambient dew point temperature.

3. Description of the Prior Art

The treatment of the respiratory tract of the young of large animals with heated, humidified air is virtually unreported in both patent and technical journal literature. Large animals is a term commonly used in the art to refer to the following animals: equine, including standardbred and thoroughbred horses, bovine, and ovine species. Approximately 9% of young horses (foals) contract pneumonia and 12% of those die as a result of the disease.

Respiratory therapy involving conditioning of the pulmonary and/or cardiovascular systems of large animals comprising delivering a saturated vapor/gas stream at a dew point temperature greater than the environmental ambient dew point temperature has not been proposed in the prior art or reported in the literature.

Inhalation therapy involving inhalation by large animals of water-vapor-saturated air at dew point temperatures from above ambient to 110° F. while administering 300 to 400 liters per minute of such air to standardbred and thoroughbred racehorses also has not been found in technical literature.

In general, prior patent and technical art refer to the administration of medicines, anesthesia, drugs, (M.A.D.), etc., to small animals such as cats, dogs, chickens and the like for the purpose of enhancing vaccinations, etc. Water vapor reportedly has been transferred into the respiratory system of small animals at temperatures equal to or lower than the normal body temperature of the animals. Therapy treatment (i.e., other than replacement of bypassed natural humidification during anesthesia or other procedures involving tracheal intubation) of the respiratory tract of animals at dew point temperatures near or above normal core body temperatures is unreported or unsuggested in the prior art.

The present invention is a drug free therapeutic treatment for respiratory disease in animals. Respiratory disease particularly foal pneumonia, is a major cause of death in foals. Over 1% of 22 foals die of pneumonia each year. Improving mucocilliary clearance can lead to reduced mortality rates.

SUMMARY OF THE INVENTION

A high humidity method and an apparatus for therapeutic of treatment of young animals are described which are useful for conditioning the respiratory, pulmonary and/or cardiovascular system in an animal. The method broadly comprises delivering a humidified stream of gas at a dew point temperature greater than the ambient dew point temperature to an animal's respiratory tract. This reduces airway water loss and if the dew point delivered is above core body temperature upon cooling produces a thin film of condensation on the walls of the entire respiratory tract from the nasal sinus to the alveoli. Retained and absorbed water thins the mucous blanket, dissolves mucous plugs, and promotes mucocilliary clearance.

A high-humidity therapy and apparatus are described which are useful for clearing pulmonary secretions and hydrating the pulmonary tract and for increasing peripheral blood circulation of foals to treat and prevent respiratory diseases.

The invention relates to apparatus and methods where the humidity level in the respiratory tracts of large animals is increased by muzzle mask administration of water-vapor saturated air to produce inspired dew point temperatures ranging from above ambient up to about 110° F. and no higher than 115° F. The present invention is a method to minimize negative inspiratory pressure and obstruction of bronchial connections to the alveoli by promoting the natural mucocilliary secretion and particulate-clearance action of the bronchial system by the prevention of airway water loss and by the hydration of airway surfaces through the administration to the upper respiratory tract of large animals of a substantially sterile, water-vapor-saturated airstream. This method of improving pulmonary hygiene helps condition the animal to achieve its maximum oxygenation efficiency through reduction of airway obstructions and hydration of airway membranes and mucous. The method also eliminates evaporative cooling from the respiratory system and, typically will increase metabolic heat rejection from other body surfaces by about 10 percent, and consequently, induces increased peripheral blood circulation.

The veterinary respiratory therapy apparatus of the present invention is particularly adapted for application of vapor-phase water in treating the upper respiratory tract of large animals with a substantially sterile, water-vapor-saturated airstream having a substantially uniform dew point/dry bulb temperature above ambient temperature and to above 110° and at flow rates less than 60 liters per minute but sufficient to match the normal inhalation flow rate of a typical young animal.

The apparatus of the invention comprises a portable electric-powered air blower, means for humidifying the air stream, a flexible delivery tube, means for conducting the humidified air without excessive condensation to a muzzle mask and means for administering the humidified air to the nasal passages of a large animal such that the dew point temperature of the inspired air can be controlled from above ambient to 110° F. The unified apparatus comprises elements that are relatively inexpensive, portable, and can be operated or maintained by individuals not having a high degree of technical expertise or horse-handling skill for pulmonary and cardiovascular conditioning of foals and other large animals.

DETAILED DESCRIPTION OF THE PREFERRED EMBODIMENTS

Figure 1:
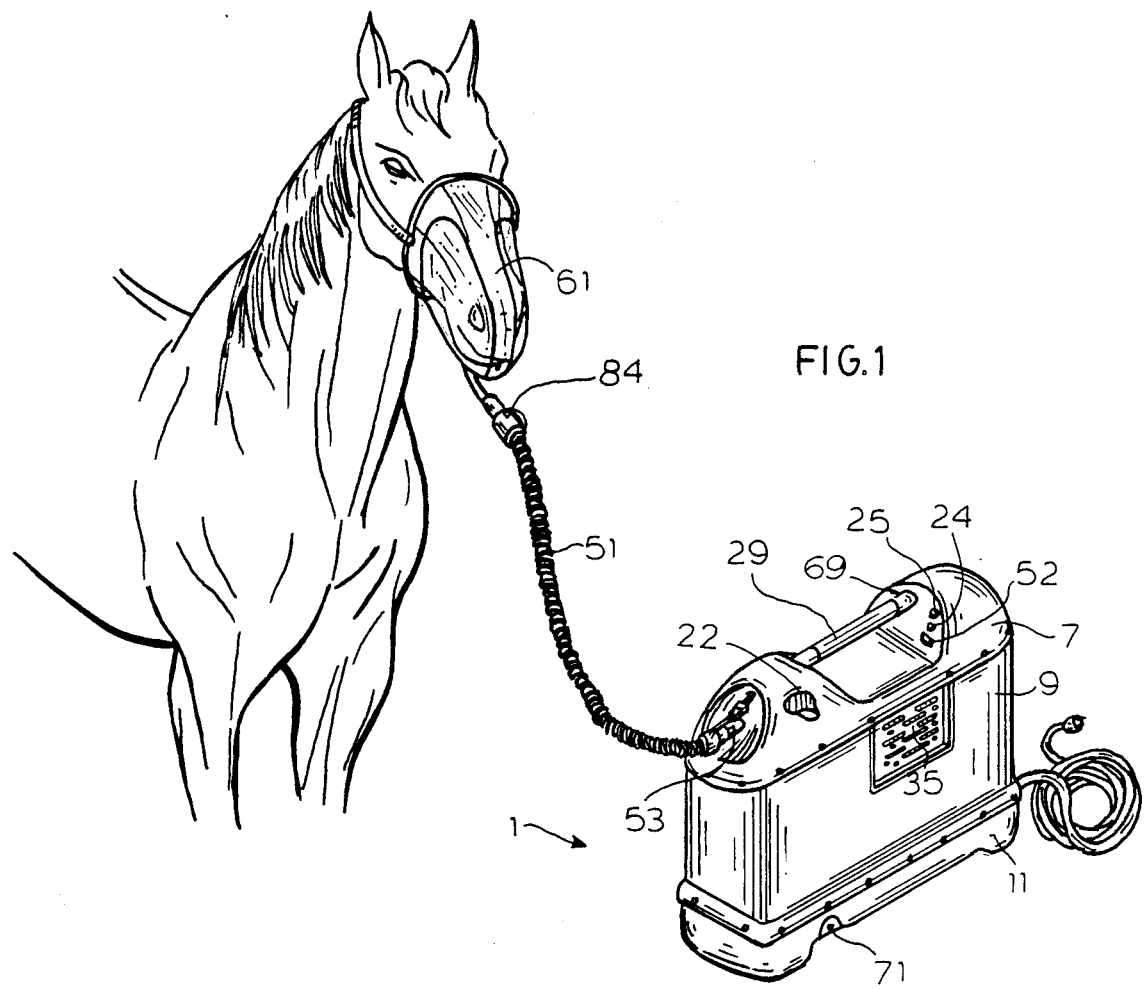
FIG. 1 is a front oblique perspective view of the right side of the portable electric powered humidifier unit showing the muzzle mask secured for the administration of a high-humidity air stream to an equine.

FIG. 1 is a front oblique perspective view of the right side of the portable electric powered humidifier unit showing the muzzle mask secured for the administration of a high-humidity air stream to an equine. Ambient air enters the cabinet 1 at atmospheric pressure, through air filter 35, exits into a delivery tube 51 after mixing with water vapor, and is delivered to the animal shown standing on the left side of the cabinet via a muzzle mask 61.

Although the apparatus as shown is designed for ambient air, it can be readily adapted to receive supplementary gas under pressure. Oxygen, nitrous oxide, and other inhaled anesthetic and therapeutic agents can be used.

Figure 4:
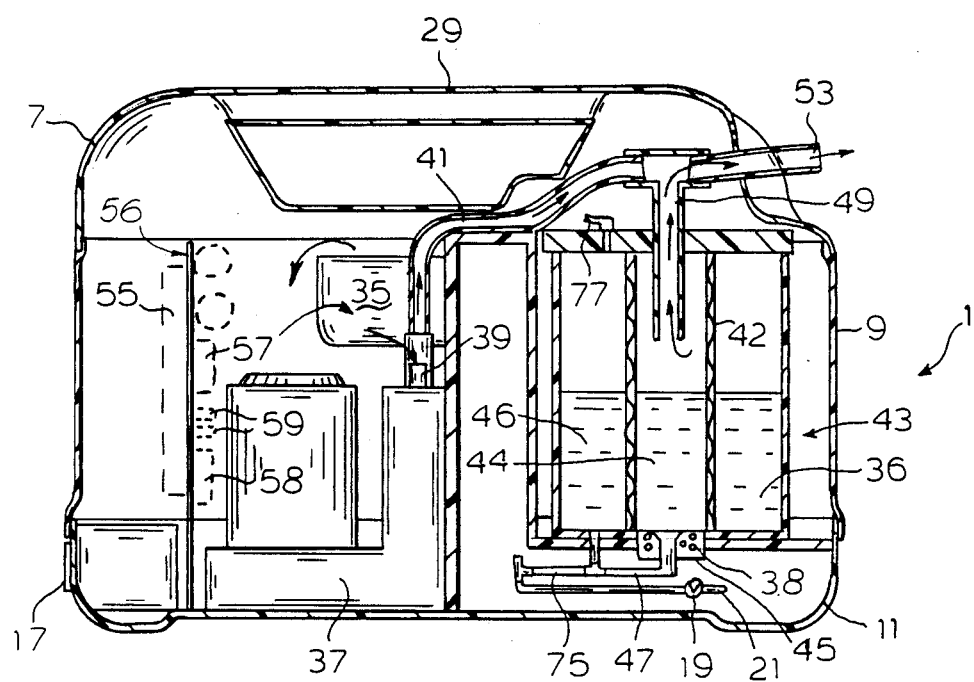
FIG. 4 is a vertical cut-away showing air flow through the right half of the apparatus.

Referring now to FIG. 4, the air enters the cabinet through air filter 35 and is drawn into the gas blower 37 through intake orifice 39 and exits via a plastic conduit 41 under positive pressure.

The air mixes with water vapor which exits water reservoir 43 through second conduit 49. The air and water vapor flows mix at the intersection of the two conduits 41 and 49 and then continue through a third conduit 53, exit the cabinet 1 and flow through the flexible plastic delivery tube 51 into the mask 61.

Figure 5:
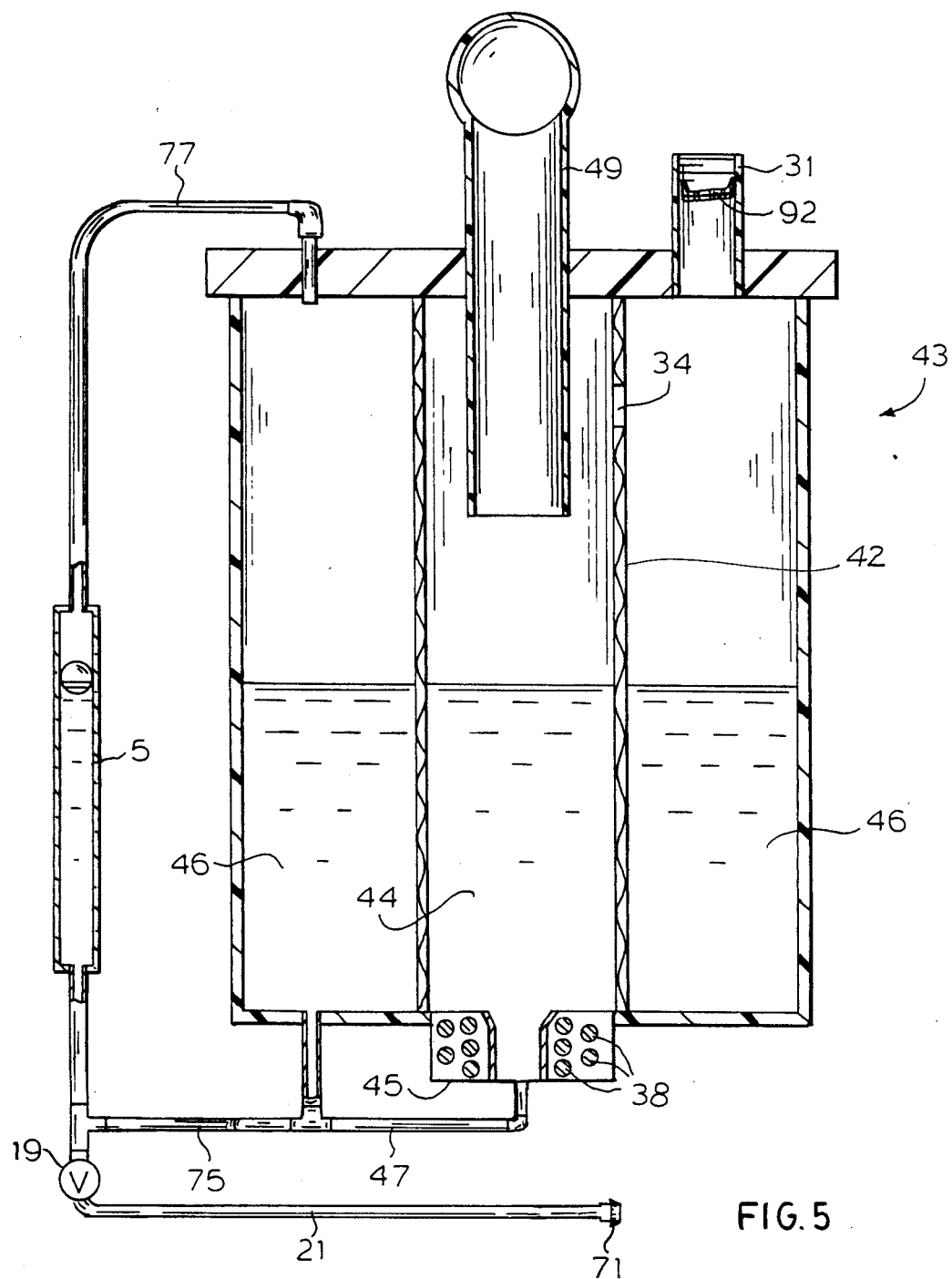
FIG. 5 is a sectional view of the humidification pot.

Referring now to FIG. 5, water enters the cabinet 1 from a liquid inlet port 31 into the outer reservoir 46 of the insulated stainless steel water reservoir 43. A plastic tube 42 coaxial with reservoir 43 divides the container into an inner reservoir 44 and outer reservoir 46. Water flows into the inner reservoir 44 through tubing 47 until the fluid levels in the two reservoirs are equal. A vent 34 near the top of the divider 42 allows the air pressure in the two chambers to equilibrate.

Water in the inner chamber is in direct contact with an electric heater 45. When the invention is switched on, electric power is fed to the heater coils 38 which are embedded in the electric heater. Water in the inner reservoir 44 is preferentially heated. The water sequestered in the inner reservoir 44 is a minor portion of the water in the container 43 and permits a fast heat up.

The electric heater 45 imparts sufficient energy to the water 36 in the interior chamber to humidify the air in the chamber. Water vapor flows into conduit 49 and then mixes with the ambient air flow and is delivered to the animal.

The conduit 49 is axially aligned with the plastic tube 42. This minimizes the effect of tilting of the cabinet 1 on the water level.

Water within the inner reservoir 44 is heated by the electric heater 45 to boiling temperature, which temperature exceeds the temperature required for pasteurization, i.e., 140° to 180° F. Pasteurizing the water serves to kill bacteria which are a source of respiratory infections. Pathogenic organisms can multiply in the unheated container 43 but will be pasteurized as they pass from chamber 46 to chamber 44 where the water is vaporized for introduction into the air on its way to the animals respiratory tract.

The delivery tube 51 is heated by the water vapor. Insulation may be added to minimize condensation of water vapor on cooling. The delivery tube may be optionally heated by electrical or water-jacket means to prevent condensation.

The electric heater 45 administers heat to the interior chamber in response to control signals from a wet-bulb temperature sensor 84 (shown in FIG. 6A) located near the exit of delivery tube 51. Should the temperature at the sensor 84 exceed a pre-determined upper limit, i.e., 115° F., a thermal switch opens thereby turning off power to the electric heater 45.

In the event that sensor 84 is disconnected and no temperature measurement can be made, the power to the heater 45 will be turned off. However, the fan 62 and the blower 37 will still operate. Thus, when sensor 84 is disconnected, unheated ambient air will be passed through the delivery tube. This air will have an additional water carrying capacity and can be used to dry the delivery tube. During such procedures, the muzzle mask is not intended to be connected to an animal.

A recessed liquid drain outlet port 71 (shown in FIG. 1) and drain valve 19 (shown in FIG. 5) are incorporated to provide a means of removing water from the container 43. To drain the water, a recessed drain lever 73 located on the left side of the cabinet (shown in FIG. 2) is rotated to open drain valve 19. Gravity forces the water through drain conduit via outlet port 71. Conduit 21 is beneath the heating container 43 and delivers the water to the drain port 71 on the right side of the cabinet away from the attendant. This design is a safety feature which prevents water from spilling on the attendant who opens the valve.

A sight tube 5 (shown in FIG. 2) on the left side of the cabinet permits the user to check the water level in the heating container 43 prior to starting treatment. The sight tube is operationally connected to the water reservoir via a conduit 75 (shown in FIG. 5). A conduit 77 permits the air pressure in the sight tube 5 and the heating container to equilibrate.

In normal operation, water in the inner reservoir 44 acts as a heat sink to keep the temperature of heater 45 below a predetermined level. When the reservoirs 44 and 46 run dry, the temperature of the electric heater 45 increases. A sensor 79 (not shown) attached to the electric heater automatically shuts the power to the heater off when the sensor exceeds a predetermined temperature. Simultaneously, an indicator light marked "Refill" located on the control panel 69 (shown in FIG. 1) will lock on.

Figure 6A:
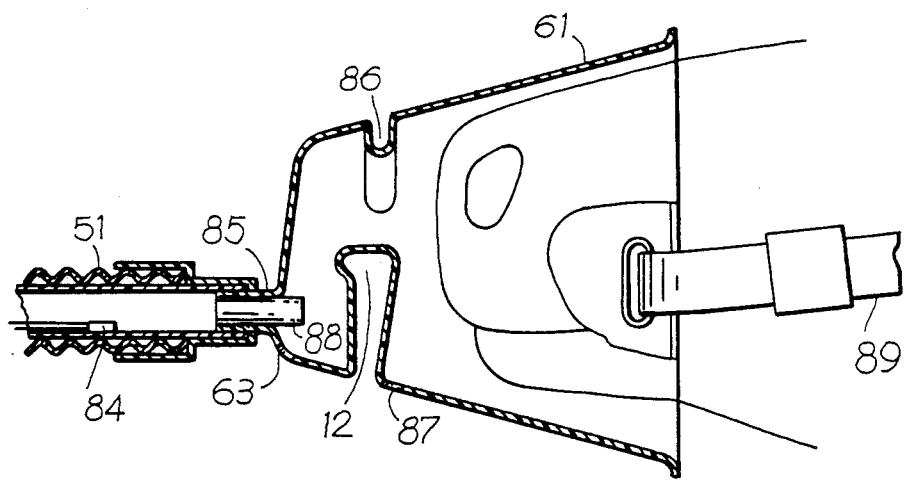
FIG. 6A is a sectional view of the mask on an equine showing connection to a delivery tube.
Figure 6B:
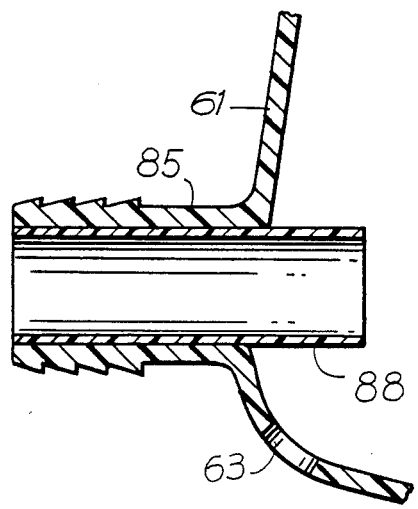
FIG. 6B is an enlarged view of the connector portion of the mask.
Figure 6C:
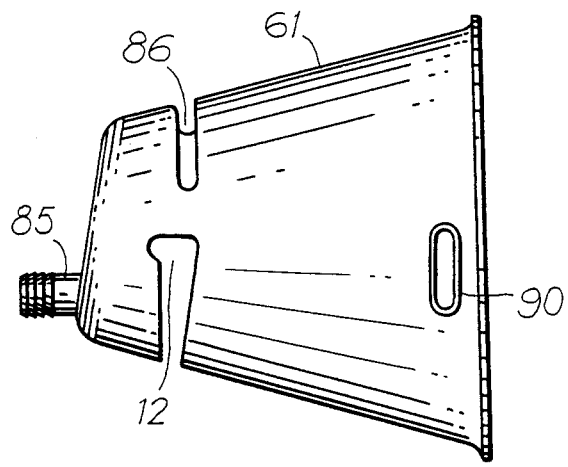
FIG. 6C is a side view of the mask.

FIG. 6A depicts a preferred configuration of a reusable, easily cleaned mask. Delivery tube 51 connects to fitting 85 which is molded into mask 61. As shown in FIG. 6B, tube 88 is inserted inside fitting 85 and protrudes into the mask. Referring to FIG. 6A, air exiting the delivery tube impinges directly on diffuser 12 which is molded into the mask to prevent direct impingement of high velocity air from the delivery tube onto the horse's muzzle.

The mask is designed to minimize the formation of aerosols from condensed water in tube 51. Flow director 86 is molded into the mask to direct humidified air flow preferentially toward the horse's nostrils in order to maximize the total amount of water vapor inspired. Diffuser 12 acts as a barrier to condensate. Excess condensate drains from the mask via port 63. Tube 88 prevents condensate from draining directly into delivery tube 51. Diffuser 12 and flow deflector 86 act in concert to direct humidified air toward the horse's nostrils. Condensate from the body of the mask and secretions from the animal drain from the mask via port 87.

Figure 6D:
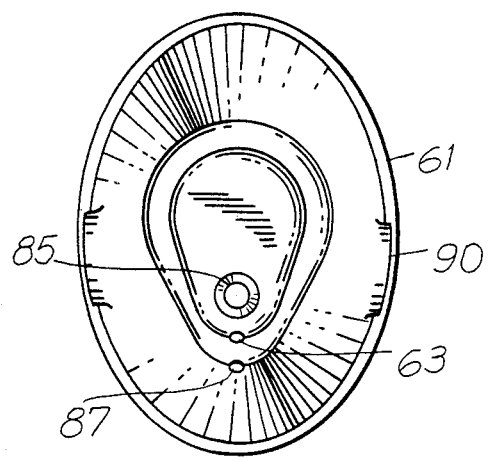
FIG. 6D is an end view of the mask.

FIG. 6D, an end view of the mask, shows its oval shape so as to fit relatively closely to the horse's muzzle. When the mask is placed on a horse, there is a relatively uniform velocity of humidified air over the nostrils, and virtually no entrained air is drawn into the mask around the horses muzzle. Drain ports 63 and 87 are positioned so as to be at a low point of the mask when the horse is standing with a lowered head, the normal position for receiving treatment.

The mask is secured to the horse by means of an adjustable strap 89 which connects to the mask via a port 90 on each side of the rear end of the mask. The strap passes behind the horse's ears and is adjusted in length to allow clearance between the end of the horses muzzle and diffuser 12.

A tracheal mask, ventilator, hood, or tent may also be used. The mask may optionally include a temperature sensor indicator (not shown) to continuously monitor the temperature within the muzzle mask 61 during the administration of therapy.

An electric circuit board 55 as shown in FIG. 4 is attached to the partition 56. Positioned on the opposite side of the partition are a transformer 57, a heat sink 58 and two solid state relays 59.

Figure 2:
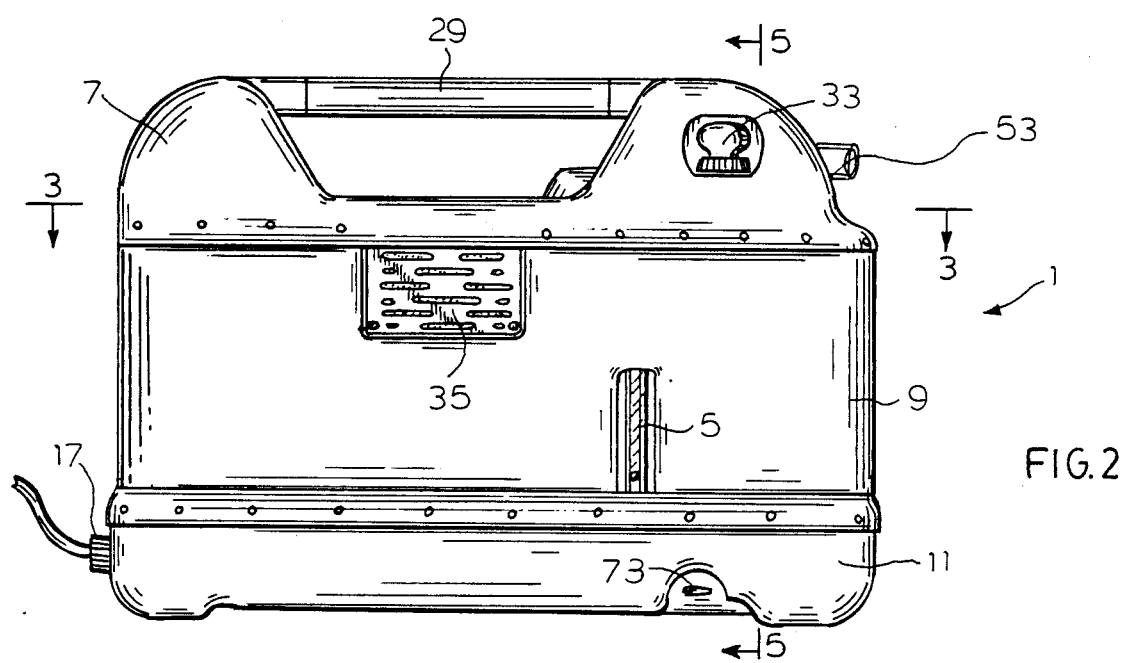
FIG. 2 is a side view of the left side of the portable electric powered humidifier unit.
Figure 3:
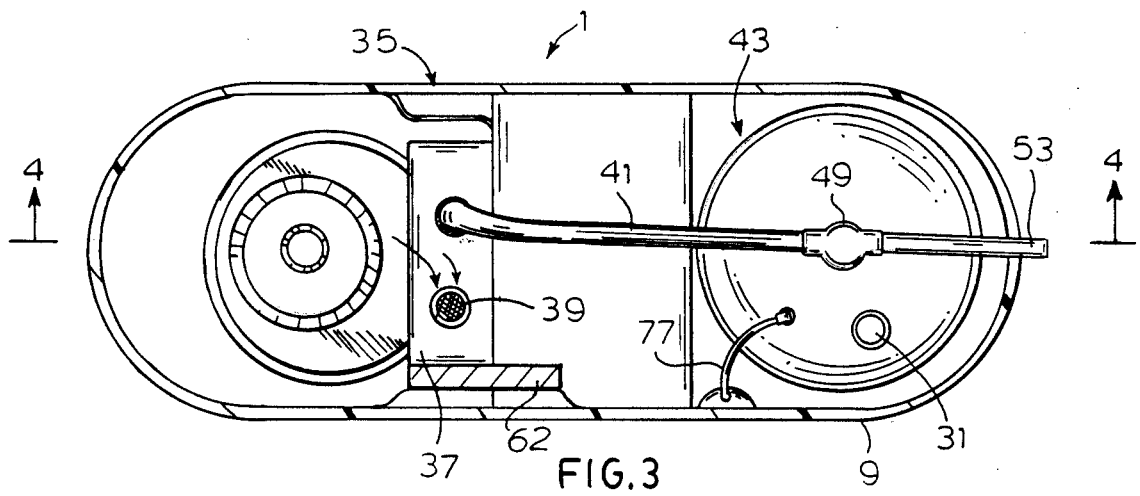
FIG. 3 is a horizontal cut-away showing the internal features of the apparatus.

The exterior of the therapy apparatus of the present invention as shown in FIGS. 2 and 3 is designed for safety. The cabinet 1 includes an upper section 7, a middle section 9, and a lower section 11.

The apparatus is double insulated and grounded. There are no exposed electrical parts. A twist lock electrical plug 17 prevents the animal or the attendant from unintentionally breaking the electrical connection. The electrical plug is removable for ease of storage and transportation. The three cabinet sections 7, 9 and 11 are vacuum formed using an acrylonitrile-butadiene-styrene copolymer, which has good impact resistance and heat resistance under normal ambient conditions. This copolymer contributes to the light weight of the apparatus, allowing it to be lifted with relative ease. The apparatus may optionally include integral wheels. However, because it is light weight, this is unnecessary.

The upper section 7 is contoured to prevent water accumulations if the apparatus is exposed to precipitation. For additional safety, the control panel 69 is waterproof and is positioned in a protected area.

The lower section 11 is water-tight since it is formed as one piece. Thus, the device can sit in water such as a puddle without wetting the interior of the device.

The apparatus in its upright position has a low center of gravity for stability. This prevents the apparatus from falling over if it is kicked by the animal or the attendant or if it is subjected to a sudden acceleration during transport.

These features are critical because of the environment of actual use. Severe service is expected as the apparatus can be easily transported throughout stables, and can be used to treat several horses on any given day.

An inlet port cap 33 (shown in FIG. 2) seals inlet port 31 to maintain container pressure, prevent contamination of the water and prevent spills during transportation. Screen 92 (FIG. 5) filters large particulates from the feed water.

A recess 22 in the upper section 7 (shown in FIG. 1) provides a convenient place for the storage of a disinfectant solution. A handle 29 is centered in the upper section for ease of transporting the cabinet 1.

The control panel 69 has a power switch 52, a test switch 24, a run/dry switch 25, and a digital temperature gauge 23 (not shown). The power switch 52 controls the power to the entire apparatus including heater 45, blower 37, fan 62 and electric control circuitry 55. The run/dry switch 25 is normally placed in the run position. In the dry position, no power is applied to heater 45, but blower 37 continues to operate. The resulting flow of ambient air through the apparatus dries condensate from delivery tube 51. A test switch 24 allows the user to substitute a known resistance for temperature sensor 84. The temperature sensed by sensor 84 is displayed on digital temperature gauge 23. When test switch 24 is closed, the gauge reading on 23 indicates whether or not the control is functioning properly. A green light (not shown) may also be on control panel 69 to indicate power is being applied to heater 45. If the temperature at the top of conduit 49 exceeds preset limits a red light (not shown) which may also be on control panel 69 turns on to indicate "fault". This temperature is sensed by a sensor (not shown) located at the top of conduit 49. A "fault" signal can be caused by loss of air flow as a result of plumbing failure, blocked conduits, or a failure of blower 37. An elapsed time indicator records the total number of hours the apparatus has been switched on. Either a "refill" or "fault" signal will shut off the power to heater 45.

EXAMPLES

The following examples illustrates the high humidity therapy treatment in accordance with the present invention of the young of large animals as an effective means of preventing and/or healing, reducing, and repairing the tissue damage done to the cells, alveoli, mucousa, nostrils, mucus membranes, nasal passages, bronchioli, etc., associated with respiratory illnesses such as pneumonia.

Example 1.

Foal was premature and contracted pneumonia. Following a relapse, treatment with high humidity was started evening of Apr. 9, 1986. On April 10, foal was up and lively all day. Resting breath rate had decreased to 36 (had been 50). Continued with 1 hour treatments through April 12. Discontinued treatments on April 14 and 15 due to temperature rise. On April 16, foal was examined by x-ray which showed pneumonia cleared except for a small spot.

This case was reported in July, 1986 Modern Horse Breeding as follows:

Thoroughbred foal born 3½ weeks prematurely developed signs of consolidated pneumonia soon after birth. Antibiotics helped, but relapse followed. Lung congestion resulting from recumbency was a contributing factor to deteriorating condition. Placed on Transpirator. By morning he was producing copious amounts of mucus. "Auscultation of the lungs revealed definite clinical improvement." Jim Prendergast, DVM. Side effect of transient temperature spikes attributed to the effort of coughing up exudate. Antibiotics discontinued at 7 weeks. Colt continuing to progress at 3 months on Transpirator and round-the-clock nursing.

Example 2.

The following case was also reported in the July 1986 issue of Modern Horse Breeding:

Foal suffering from Corynebacterium equi did not respond. Tried rifampin/erythromycin combination therapy in conjunction with Transpirator. According to the veterinarian, "Three days after treatment, the foal was 100% better. I find it hard to believe it was just the antibiotics. You could near him start to break up. And the material that came out of his nose-gobs of wet dark mucus. One other amazing thing: the foals actually seek out the treatment.

Example 3.

Two treatments of foal with anoxia brain injury at birth. Favorable response both times. After first treatment, foal got up on its own for the first time and appeared to show better pupil reflex to light. Foal's temperature dropped 1° F. during treatment. Foal subsequently died due to prior problems.

Example 4.

The following results were reported by a doctor of veterinary medicine at the University of Minnesota:

"Twelve foals with a clinical history of bilateral nasal discharge, initial fevers from 103°–105° F., sibilant sounds, rales, depression, lethargy, poor appetite and activity, increased with blood cell count to 14–25,000 cbc and 60–80% neutrophils were placed on antibiotics. The duration of treatment ranged from 8–10 days with and average of 14–18 days. Fever persisted for 7–10 days. Nine of these foals suffered relapse approximately 10 days after they were deemed to have recovered. Three of the sickest were placed on a nigh humidity treatment regime consisting of 60 minutes of treatment per day at a dew point of 105° F. and a flow greater than their peak inspiratory flow. Tranquilizers were administered at first use, but then were discontinued after it was found that the foals would stand quietly while receiving treatment via muzzle mask. Approximately 30 minutes after treatment, they coughed up copious amounts of secretions. Fever subsided and temperatures were normal the next day. Lung sounds improved dramatically after each use. Four more foals were treated with humidity therapy. The duration of treatment for the total of seven foals treated ranged from 5–7 days vs. the 8–30 days for non-treated foals. Fever subsided in one day vs. 7–10 days."

What is claimed is:

1. A method for the therapeutic treatment of a young veterinary animal's respiratory tract comprising the step of continuously delivering to the young veterinary animal's respiratory tract a humidified stream of gas at a dew point temperature which is greater than the ambient dew point temperature at flow rates exceeding the veterinary animal's peak resting inhalation rate to condition the veterinary animal's respiratory, pulmonary and cardiovascular system.

2. The method of claim 1 wherein the step of delivering the humidified stream of gas further comprises delivering of the humidified stream of gas to a foal.

3. The method of claims 1 or 2 wherein the step of delivering the humidified stream of gas further comprises delivering a humidified stream of gas in which the dew point temperature is also greater than the normal body temperature of the veterinary animal.

4. The method of claims 1 or 2 further comprising the step of adding a sedating agent to the stream of gas thereby preventing dehydration of respiratory and pulmonary airways and preventing water loss from the airway.

5. The method of claims 1 or 2 wherein the conditioning provided by the step of delivering the humidified stream of gas comprises increasing the peripheral blood circulation of the veterinary animal to warm-up without unnecessarily depleting energy and oxygen reserves.

6. The method of claims 1 or 2 wherein the step of delivering the humidified stream of gas further comprises delivering the stream of gas to a veterinary animal suffering from bronchitis to condition the veterinary animal's bronchi wherein the stream of gas deposits water to soothe inflamed tissue thereby preventing water loss from the veterinary animal's respiratory tract allowing the animal to breath more freely.

7. The method of claims 1 or 2 wherein the step of delivery the humidified stream of gas further comprises delivering the stream of gas to a veterinary animal suffering from a sinus infection to condition the veterinary animal's sinus cavities wherein the stream of gas promotes opening and draining thereby increasing the blood flow in said infected sinus to promote healing.

8. The method of claims 1 or 2 wherein the step of delivering the humidified stream of gas further comprises delivering the stream of gas to a veterinary animal suffering from an allergy wherein the stream of gas delivers filtered gas to the veterinary animal to facilitate mucous flow and promote the removal of irritants in the respiratory tract.

9. The method of claims 1 or 2 wherein the step of delivering the humidified stream of gas further comprises delivering the stream of gas to a veterinary animal suffering from exercise-induced pulmonary hemorrhage to condition the veterinary animal's respiratory tract wherein the stream of gas deposits water thereby thinning the mucous blanket, dissolving mucous plugs and promoting mucocilliary clearance.

10. The method of claims 1 or 2 wherein the step of delivering the humidified stream of gas further comprises delivering the stream of gas to a veterinary animal suffering from pneumonia to condition the veterinary animal's lungs wherein the stream of gas promotes mucocilliary clearance of fluids thereby increasing the blood flow in the pulmonary system.

11. The method of claims 1 or 2 wherein the step of delivering the humidified stream of gas further comprises delivering the stream of gas to a veterinary animal suffering from airway obstruction wherein the stream of gas deposits water on the walls of the respiratory tract thereby thinning the mucous blanket, dissolving mucous plugs, and promoting mucocilliary clearance.

* * * * *